(12) United States Patent
Otsuki et al.

(10) Patent No.: US 6,714,301 B2
(45) Date of Patent: Mar. 30, 2004

(54) SPECTRAL ELLIPSOMETER WITHOUT CHROMATIC ABERRATIONS

(75) Inventors: Kunio Otsuki, Kyoto (JP); Yutaka Saijo, Kyoto (JP)

(73) Assignee: Horiba, Ltd., Kyoto (JP)

( * ) Notice: Subject to any disclaimer, the term of this patent is extended or adjusted under 35 U.S.C. 154(b) by 89 days.

(21) Appl. No.: 10/004,250

(22) Filed: Oct. 23, 2001

(65) Prior Publication Data

US 2002/0126284 A1 Sep. 12, 2002

(30) Foreign Application Priority Data

Oct. 25, 2000 (JP) ........................................ 2000-325362

(51) Int. Cl.[7] .............................. G01J 4/00; G01B 11/06; H01J 40/14
(52) U.S. Cl. .................... 356/369; 356/365; 356/368; 356/631; 356/632; 250/225
(58) Field of Search ........................ 356/369, 364–368, 356/630–631, 632; 250/225

(56) References Cited

U.S. PATENT DOCUMENTS

| | | | | |
|---|---|---|---|---|
| 3,904,293 A | * | 9/1975 | Gee ............................. | 356/369 |
| 5,166,752 A | * | 11/1992 | Spanier et al. ............... | 356/369 |
| 5,581,350 A | * | 12/1996 | Chen et al. .................. | 356/369 |
| 6,307,627 B1 | * | 10/2001 | Vurens ......................... | 356/369 |
| 6,486,951 B2 | * | 11/2002 | Hirosawa et al. ........... | 356/369 |

* cited by examiner

Primary Examiner—Russell Adams
Assistant Examiner—Magda Cruz

(57) ABSTRACT

A spectral ellipsometer includes a light incident optical system for focusing a incidence spot of polarized light of multi-wavelengths onto a sample surface. A detecting optical system receives the reflected light influenced by the sample surface so that the amount of change in an elliptical polarization will be characteristic of the sample surface. A spherical prism polarizer is employed in the light incident optical system having complimentary curved light incident and light exit surfaces to enable the focusing of the incident light so that each of the ray traces of the range of wavelengths are focused at the same position on the sample surface.

5 Claims, 5 Drawing Sheets

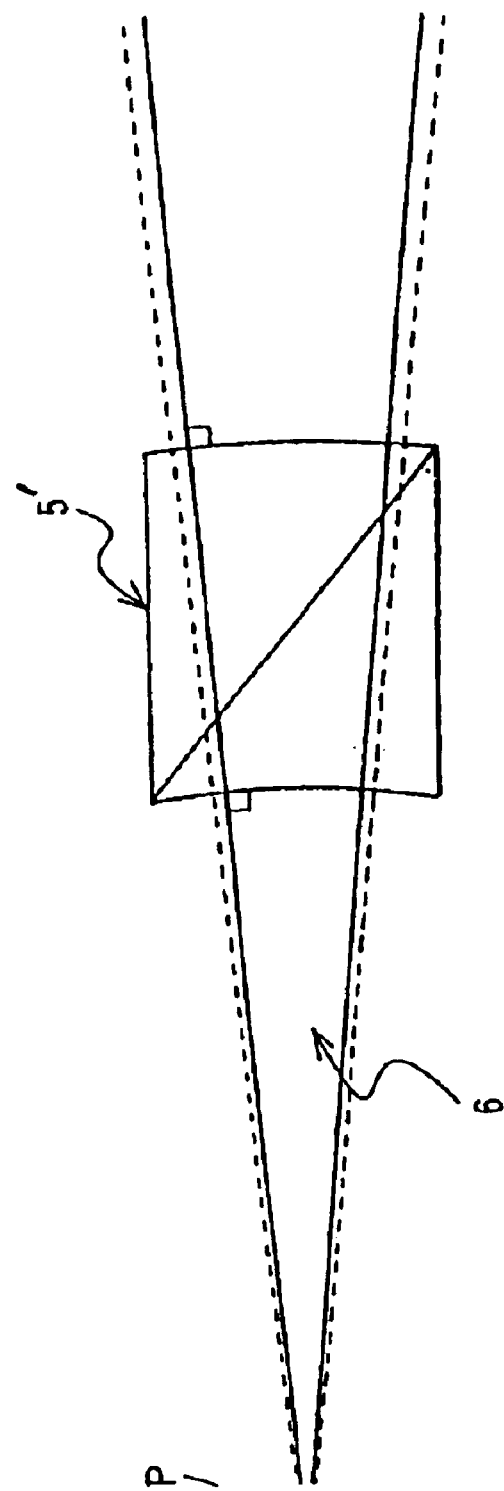

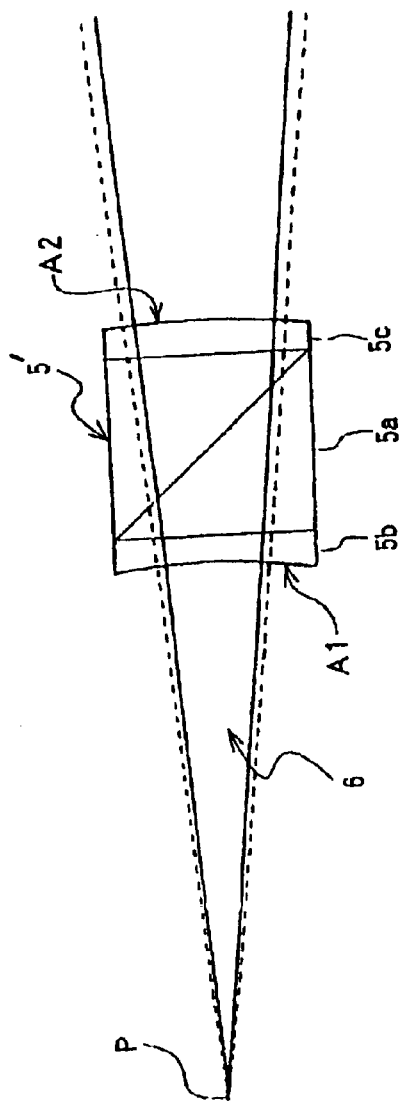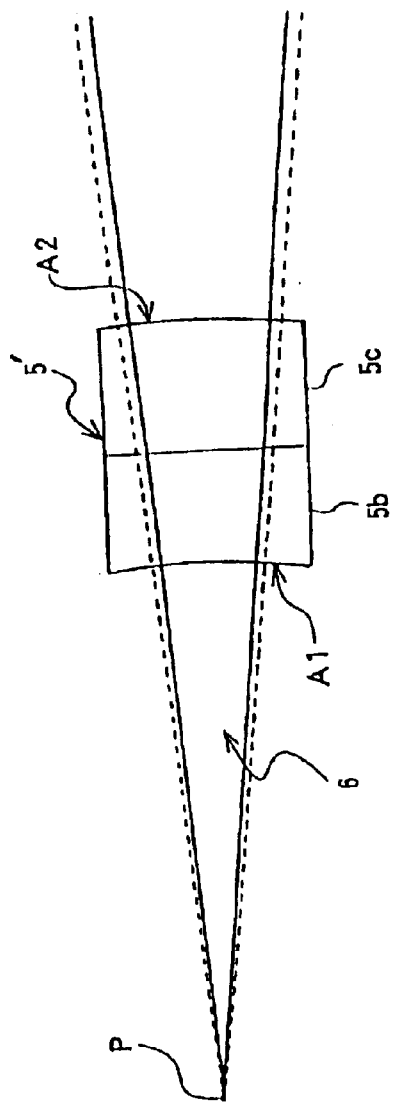

SPECTRAL ELLIPSOMETER WITHOUT CHROMATIC ABERRATIONS

BACKGROUND OF THE INVENTION

1. Field of the Invention

The present invention relates to a spectral ellipsometer for observing changes in the polarized conditions of light reflected off a surface of a test substance to permit the measuring of optical constants, such as index of refraction, and the extinction coefficient of a sample. When a thin film layer is present on the surface of the test substance, measurements of film thickness and optical constants can also be achieved, and more particularly, the provision of improved output signals that address chromatic aberrations.

2. Description of Related Art

Referring to the measurement system shown in FIG. 4, a directed light beam from a source of light 2 is folded in an optical system 4 and directed to a polarizing prism 5 to output a linearly polarized beam of light 6 to contact the surface 8a of a sample 8 on a sample station 7. The sample 8 can have a surface with a thin film and the polarized conditions of the reflected light beam 10 will change, depending on the thickness of the thin film, the index refraction and extinction coefficient of the thin film. This change in the polarized condition of the testing light beam is due to the fact that a difference in reflected light exists between P polarization and S polarization, depending on the respective shifts in phase of reflection and the reflection coefficient. As a result, it is possible to obtain the thickness of the thin film or the index of refraction of the sample surface 8a upon measuring the amount of change in polarization of the reflected light and performing certain predetermined analytical calculations. The reflected light beam 10 can be subject to a modulator 12 and analyzer 13 and a folding detecting optical system 9 for directing the reflected light to an optical fiber 14 to input signals to the spectroscope 11.

As the miniaturization of semiconductor products advances, there are additional requirements to evaluate the film qualities of ultra-thin films in numerous fields, including the manufacturing of semiconductor components. In the semiconductor field, gate oxide films and low absorption films have been increasingly thinner in the new generation of semiconductor devices. Additionally, there are requirements to accurately evaluate multi-layered structures that are employed in flash memories wherein oxide films and nitride films of silicon are alternately laminated. Additionally, multi-layered films are also formed on SOI wafers and the like.

This industry is also requiring light measuring instruments, such as spectral ellipsometers, to be capable of performing highly accurate measurements over a wide range of wavelengths ranging from ultraviolet to visible to infrared radiation. Such instruments must be further capable of performing measurements of the dependency of thin film properties on such variable wavelengths. In the conventional spectral ellipsometers that are provided with a polarizer for changing the light of a wide range of wavelengths into inear polarization, usually a prism will serve as a polarizer since it may be used in a wide range of wavelength regions from visible light to the ultraviolet region. Additionally, the prism assists in the optical quenching ratio, transmittance and similar features.

Generally, such a prism has a thickness ranging from approximately 10 mm to several tens of mm. As such, it is not possible to focus the optical axes of a wide variety of wavelength regions onto one spot, owing to differences, in, for instance, the indices of refraction with respect to wavelengths of light when reducing a beam diameter. As a result, a drawback of increased chromatic aberrations, such as shown in FIG. 5, can occur wherein a depth or zone of focus will result, such that a focusing position of Q2 of a longer wavelength will have its focus position extending further when compared to a focusing position on the optical axis of Q1 of a light having a shorter wavelength. Thus, in this context, the term "chromatic aberration" indicates differences in indices of refraction only to wavelengths, that is, aberrations resulting from dispersion (defects caused in cases where an image forming system does not satisfy conditions for Gauss image formation).

There is still demand in the prior art to address these issues as requirements of greater accuracy is being imposed upon measuring instruments such as spectral ellipsometers.

OBJECTS AND SUMMARY OF THE INVENTION

The present invention addresses the issues of chromatic aberrations by providing a spectral ellipsometer in which it is possible to easily focus all the optical axes of multiple wavelengths onto one spot by means of a relatively inexpensive improvement.

The spectral ellipsometer of the present invention includes a source of light and an optical system for directing light of multiple wavelengths to an optical element for receiving the multiple wavelength light and focusing the multiple wavelength light onto a single spot on a sample surface. A detecting optical system receives the multiple wavelength light after contact with a sample surface and it is able to process it to an output signal providing the desired information. The detecting optical system can accurately receive and transmit any change in polarization in the elliptical polarization light reflected by the sample surface. The optical element that is placed in the light incidence optical system can be a prism with a particular shape for a light incidence surface and a light exit surface, both of which can be curved so that the light is orthogonal with respect to a progressing direction of the respective directions of incident and outgoing light thereby providing a spherical prism whose curved surfaces address the range of wavelengths that are incident upon the spherical prism.

The present invention provides not only an improved spectral ellipsometer, but also a method of ensuring the focusing of light of multiple wavelengths onto a single spot on the sample surface. The light incident surface and light exiting surface of the spherical prism will, in a macroscopic sense, be orthogonal with respect to all the optical axes of the incident wavelength light so that it will be possible to substantially eliminate the phenomena of refraction of incident light and to focus across a wide range of wavelengths, all ray traces onto one spot on the sample surface to thereby prevent occurrence of chromatic aberrations.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 2 is a schematic cross-sectional view illustrating a condition wherein the ray traces of different wavelengths are focused onto one spot by a spherical prism of the present invention;

FIG. 3a is a schematic view of an embodiment of a spherical prism of the present invention;

FIG. 3b is a schematic view of another embodiment of a spherical prism of the present invention;

DETAILED DESCRIPTION OF THE PREFERRED EMBODIMENT

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein to specifically provide a spherical prism to reduce chromatic aberrations in a spectral elliptometer.

Figure 1:
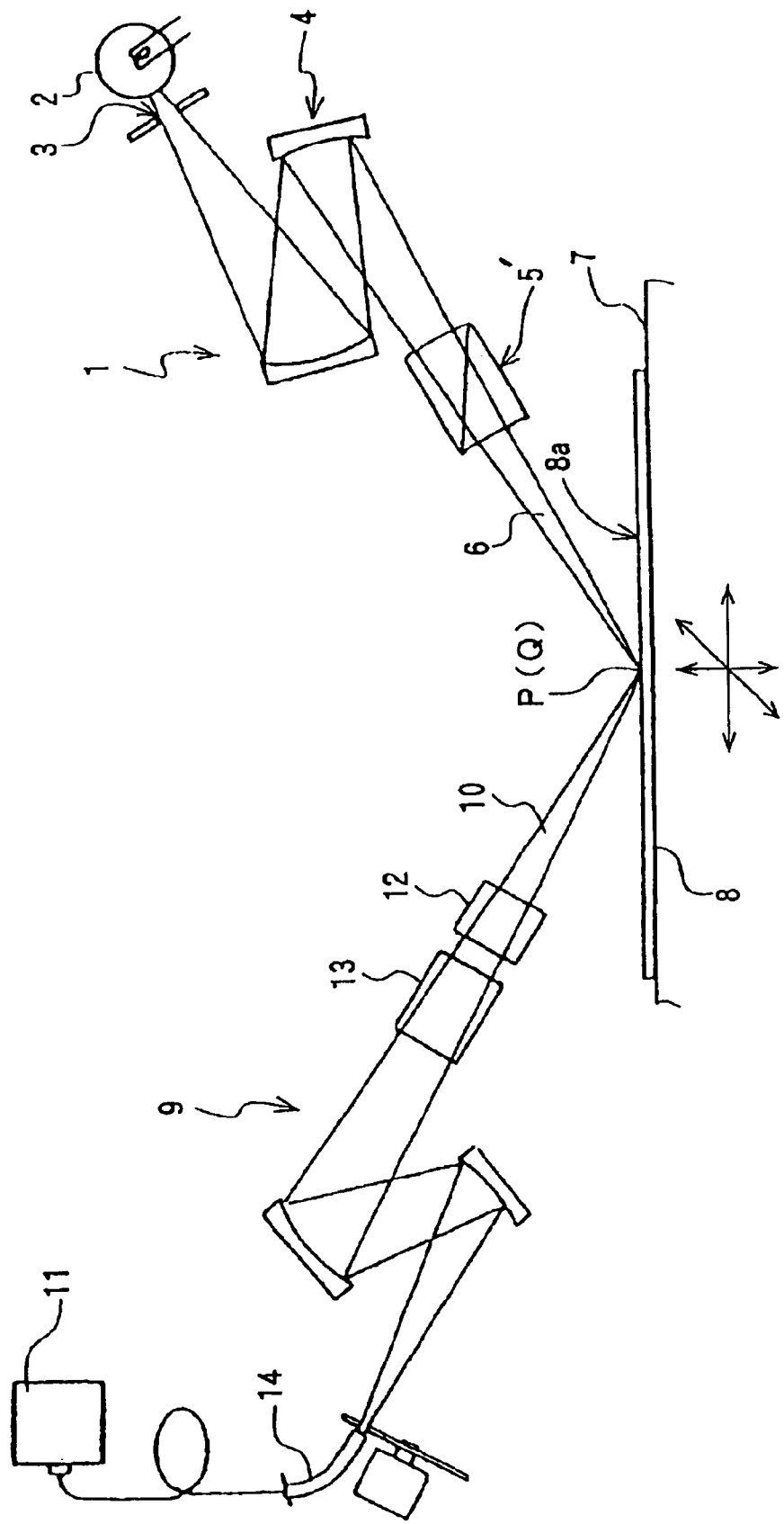
FIG. 1 is a schematic view of a spectral ellipsometer of the present invention.
Figure 4:
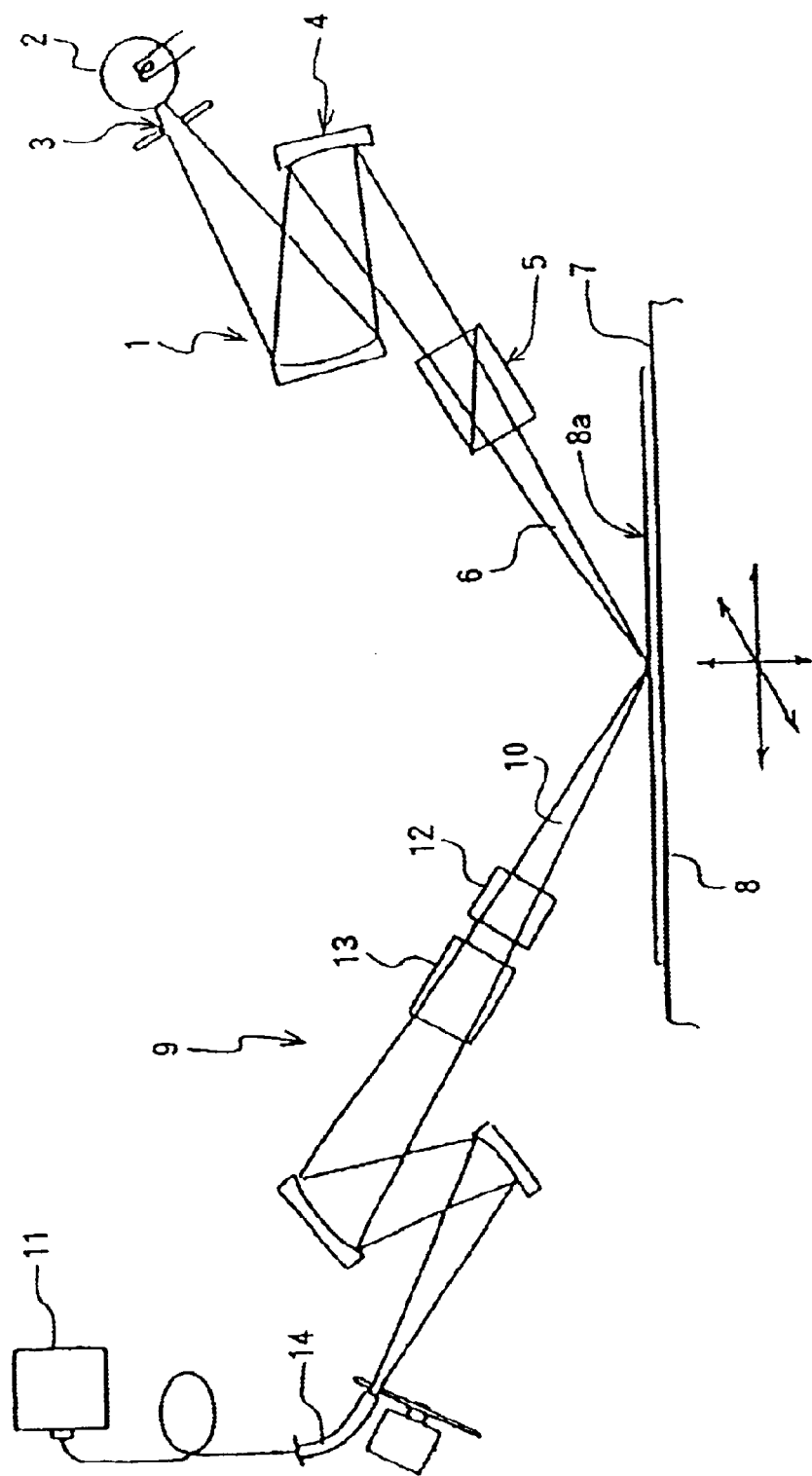
FIG. 4 is a schematic view of a conventional spectral ellipsometer.
Figure 5:
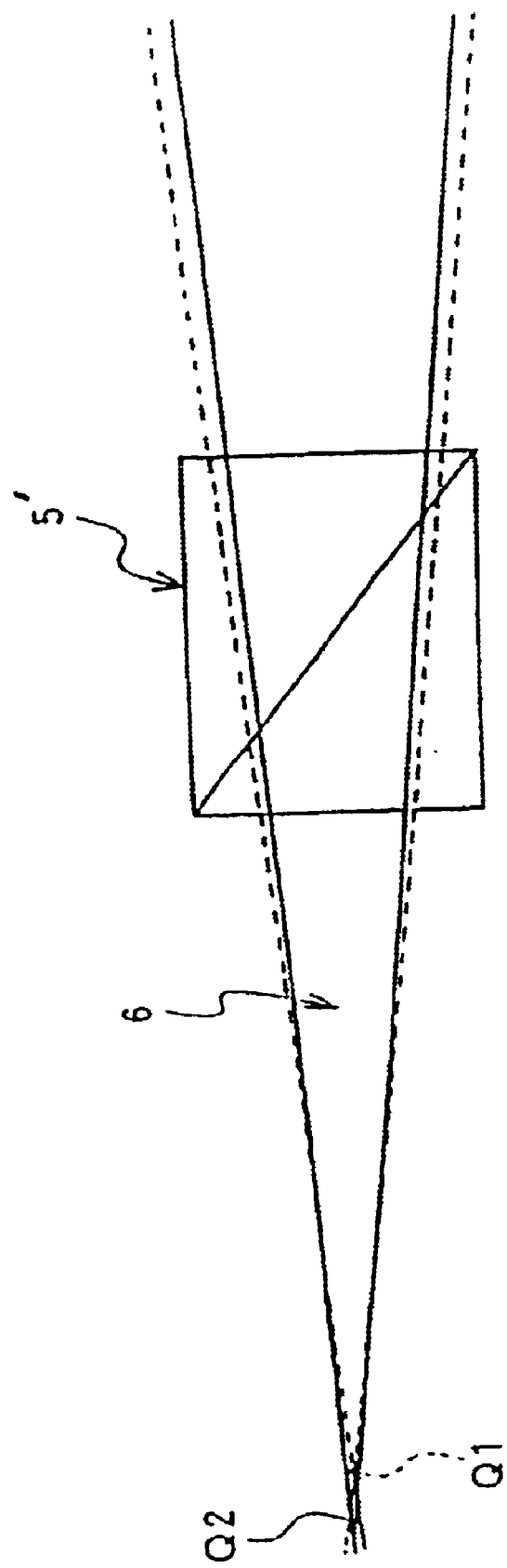
FIG. 5 is a schematic view illustrating a condition of refraction of the ray traces with a conventional prism.

Referring to FIG. 1, a first embodiment of a spectral ellipsometer utilizing a spherical prism in accordance with the present invention is disclosed. Reference numbers that are common to other figures will be used in describing FIG. 1. A light incident optical system 1 can relay the light from a white color or multi-wavelength light source 2, such as an xenon lamp or similar light source for providing a multi-wavelength region of light, for example, 190 nm to 830 nm, is provided. A slit 3 with an aperture can define the shape of the light, while a beam reducing optical system which can comprise, for example, a pair of concave reflecting lens surfaces 4, is capable of directing the light in a converging manner to enter the prism 5' which serves as a polarizer for maintaining a polarizing direction constant.

The light incident optical system 1 functions to reduce the emitted light of multiple wavelengths from the light source 2 to a spot, incident from an oblique angle, onto a sample surface 8a of a sample 8. The light 6 that is contacting the sample surface 8a has a linear polarization of a pre-determined polarizing direction as a result of transmission through a spherical prism 5'. The sample 8 is placed on a movable stage 7 which can be driven in three dimensional directions, namely, the horizontal X and Y directions and an orthogonal Z direction. The sample 8 can be held by a vacuum maintained on the surface of the stage 7, for example, through a series of apertures as is known in this field.

The prism 5' is a spherical prism with shapes of a light incident surface and light outgoing surface of curved con-figurations that are complimentary to the converging light beam from the optical system 1. The curved surfaces are orthogonal with respect to a progressing direction of the respective directions of incident and outgoing light as shown in FIG. 1.

Thus, the incident light of a plurality of wavelengths that has been transmitted from the white light source 2 is reduced in beam diameter by the beam reducing optical system 4 and is polarized in a predetermined direction by the spherical prism 5' that serves as the polarizer. By arranging the prism 5' to be spherical, incident light and outgoing light or exit light from the spherical prism 5' will become orthogonal to all the optical axes of the range of wavelengths of the incident light as illustrated in FIG. 2. It is accordingly possible to substantially eliminate the phenomena of refraction of incident light and to focus the respective ray traces of each optical axis for each of the wavelengths within a range of wavelength of the incident light onto a single spot Q. This approach substantially eliminates any occurrence of chromatic aberrations. The light reflected from the sample surface 8a will become an elliptical polarization having an amplitude and phase that are indicative of the physical properties of the sample 8 or the sample surface 8a. Thus, the incident light that has a linear polarization 6 will be changed into an elliptical polarization 10 which will then enter a photo-elastic modulator 12 to undergo a phase modulation and then thereafter enter into an analyzer 13. The analyzer 13 will transmit the converging light into the detecting optical system 9 which again includes a pair of concave reflecting lens surfaces to converge the light so that it will focus on the entrance of an optical fiber 14. The optical fiber 14 will then transmit the light signal into the spectroscope 11 to be converted into electrical signals for subsequent computation by an algorithm to provide an output measurement in a known manner.

While the photo-elastic modulator 12 is typically consti-tuted of a glass substrate or bar that can receive a periodi-cally imposed stress, for example, imposed by piezo electric elements. It is also possible to form the elliptical polarization 10 into a linear polarization by using a rotary polarizer. It is further possible to provide a photoelastic modulator 12 or a rotary polarizer within the light incident optical system.

While the spherical prism 5' is formed as a uniform molded body in the first embodiment, it is alternatively possible to construct the spherical prism 5' as a combined body of a prism body 5a having a rectangular parallel piped body and joined thereto to prism bodies 5b and 5c, respectively, having a concave curved surface and a convex curved surface A1 and A2 around the center P as illustrated in FIG. A. Alternatively, the spherical prism 5' can be formed as a combination of a pair of prism bodies 5b and 5c as shown in FIG. 3b again having a concave curved surface and a convex curved surface A1 and A2, respectively, around the center P.

As can be appreciated, the advantages of the present invention can be also utilized other than in the semiconduc-tor field so that measurements can be made on other items such as for example, a liquid crystal structure.

By setting the incident and outgoing surfaces of the prism 5' as curved surfaces, it is possible to provide in a spectral ellipsometer the capability of easily focusing all the ray traces and optical axes of a range of wavelengths onto one spot and thereby effectively addressing the issue of chro-matic aberrations. Such arrangement permits the perfor-mance of precise and highly accurate measurements by using a spectral ellipsometer employing multi-wavelengths.

In operation, a predetermined range of wavelengths can be directed in a convergent manner to a spherical prism that has been designed with curved and complimentary surfaces to enable a focusing of each of the wavelengths onto a single spot at an oblique angle to a sample surface. The reflected polarized light can thereby be detected and computations can be made based upon the characteristic influence of the sample surface as a linear polarized light becomes an elliptical polarization having amplitude and phase changes that are indicative of the physical properties of the sample.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a spectral ellipsometer, which includes a light incidence optical system for achieving spot incidence of polarization light of multi-wavelengths onto a sample surface and a detecting optical system for outputting information concerning the sample surface based on an amount of change in elliptical polarization reflected by the sample surface, the improvement comprising a prism polarizer employed in the light incidence optical system with a curved light-incident surface and a curved light-outgoing surface that is orthogonal with respect to a progressing direction of the respective direction of incident and outgoing light.

2. A method of optically determining the characteristics of a sample surface, comprising;

providing a multi-wavelength light;

polarizing the multi-wavelength light including a spherical polarizing prism;

directing the polarized multi-wavelength light to focus at an oblique angle on a single point on a sample surface;

measuring the reflected polarized light from the sample surface, and determining the characterization from the change in polarization determined in the measured light.

3. The method of claim 2, wherein the spherical polarizing prism has an incident convex surface and an exiting concave surface.

4. In a spectral ellipsometer having a source of multi-wavelength light, an optical system for directing the light, and a detecting optical system for receiving light after contact with a sample surface, the improvement comprising:

a spherical prism for receiving the multi-wavelength light directed from the optical system and focusing the multiple wavelength light onto a single spot on the sample surface.

5. In a spectral ellipsometer having a source of multi-wavelength light, an optical system for directing the light, and a detecting optical system for receiving light after contact with a sample surface, the improvement comprising:

a polarizing prism with at least one curved surface for receiving the multi-wavelength light directed from the optical system and focusing the multiple wavelength light onto a single spot on the sample surface.

* * * * *